United States Patent
Godwin et al.

(10) Patent No.: US 9,462,807 B2
(45) Date of Patent: Oct. 11, 2016

(54) DIFENOCONAZOLE STEREPOSPMERIC COMPOSITION WITH REDUCED PHYTOTOXICITY

(71) Applicant: Syngenta Participations AG, Basel (CH)

(72) Inventors: Jeremy Robert Godwin, Stein (CH); Alexander Mark Heming, Stein (CH); Christian Lothschuetz, Münchwilen (CH); Peter Schneiter, Stein (CH); Wolfgang Stutz, Muenchwilen (CH)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 14/765,212

(22) PCT Filed: Jan. 27, 2014

(86) PCT No.: PCT/EP2014/051528
§ 371 (c)(1),
(2) Date: Jul. 31, 2015

(87) PCT Pub. No.: WO2014/118127
PCT Pub. Date: Aug. 7, 2014

(65) Prior Publication Data
US 2015/0366203 A1  Dec. 24, 2015

(30) Foreign Application Priority Data
Feb. 4, 2013 (GB) .................... 1301979.9

(51) Int. Cl.
| | |
|---|---|
| *A01N 25/00* | (2006.01) |
| *A01N 43/653* | (2006.01) |
| *A01N 43/64* | (2006.01) |
| *A61K 31/41* | (2006.01) |
| *C07D 405/06* | (2006.01) |

(52) U.S. Cl.
CPC ........... *A01N 43/653* (2013.01); *C07D 405/06* (2013.01)

(58) Field of Classification Search
None
See application file for complete search history.

(56) References Cited

U.S. PATENT DOCUMENTS 5,266,585 A   11/1993  Hubele et al.
2010/0184816 A1   7/2010  Hauser-Hahn

FOREIGN PATENT DOCUMENTS

WO   2007031309 A2   3/2007
WO   2007065843 A2   6/2007

OTHER PUBLICATIONS

Jing Li et al—Simultaneous enantioselective determination of triazole fungicide difenoconazole and its main chiral metabolite in vegetagbles and soil by normal-phase high-performance liquid chromatography—Anal Bioanal Chem 2012 (2017-2031).
241 Difenoconazole—XP003032203—Pesticide Manual vol. 12 Jan. 9, 2000 p. 290).
Ying Zhou et al—Enantiomer Separation of Triazole Fungicides by High-Performance Liquid Chromatography—Chirality 2009 (pp. 421-427).
Nithyameenakshi et al—Investigations on Phytotoxicity of Two New Fungicides, Azoxystrobin and Difenoconazole—American Journal of Plant Physiology 1 (1) 2006 (pp. 89-98).
International Search Report, dated May 16, 2014 for International Application No. PCT/EP2014/051528.

*Primary Examiner* — Alton Pryor
(74) *Attorney, Agent, or Firm* — James Cueva

(57) ABSTRACT

The present invention relates to a composition and its use in a method for safening the phytotoxic effect of difenoconazole on a plant or plant propagation material. More specifically the composition comprises difenoconazole characterised in that least 40% by weight of said difenoconazole is the 2R, 4S isomer depicted as formula (Ib): and wherein at least 95% by weight of the remaining difenoconazole is the 2S, 4S isomer depicted as formula (Id):

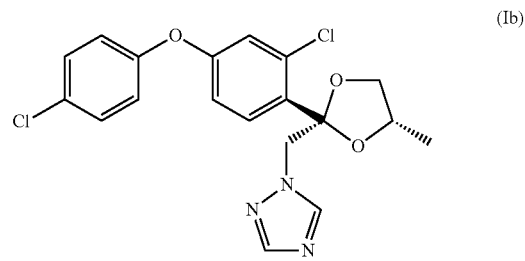

(Ib)

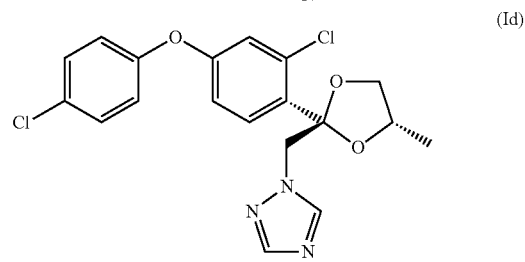

(Id)

11 Claims, No Drawings

DIFENOCONAZOLE STEREPOSPMERIC COMPOSITION WITH REDUCED PHYTOTOXICITY

RELATED APPLICATION INFORMATION

This application is a 371 of International Application No. PCT/EP2014/051528, filed Jan. 27, 2014, which claims priority to GB1301979.9, filed Feb. 4 2013, the contents of which are incorporated herein by reference herein.

The present invention relates to a fungicidal composition which comprises difenoconazole in a fungicidally effective amount whereby when said composition is applied to a plant or propagation material said composition has a reduced phytotoxic effect on said plant or propagation material.

It is known that some plant protecting agents, such as fungicides, can have a phytotoxic effect on crop plants. For example, F. Montfort et al., Pesticide Science 46(4), 1996, 315-322, report that the use of azole fungicides, such as triticonazole, for the treatment of seed and crop plants may have an adverse effect on plant growth. WO2008/155416 describes use of gibberellin for reducing or preventing the phytotoxic effect of azole fungicides or of azole fungicides used in combination with anilide fungicides, primarily for seed treatment.

WO2007/065843 describes use of gibberellin as a safener for azole fungicides, specifically for the purpose of reversing the stunting effect and the delayed or impeded germination. These prior art solutions utilize the addition of a substance to the composition containing the azole fungicide.

Zawisza et al. Progress in Plant Protection, Vol. 44(2), 2004 describes the separation of the cis and trans isomers via thin-layer chromatography and the subsequent testing of the cis and trans isomers for fungicidal efficacy only.

A particular type of phytotoxic effect that can limit the usefulness of some fungicides is chlorosis and desiccation of leaves which is manifested as a yellowing and/or browning of the leaves of the plant to which the fungicide is applied, which in some cases may occur when the fungicide is used at optimal levels for controlling fungi. Reducing the rate of fungicide application will normally reduce the leaf yellowing and/or browning effect, but then the fungicide will not be present at an optimal rate for controlling the fungi. There is a need for methods of preventing or at least mitigating the phytotoxic effects such as leaf-yellowing and/or browning effect mediated by fungicides in order to maximise the potential of their fungicidal efficacy. The present invention seeks to address these needs.

There is a continuing need to find methods of protecting plants from phytopathogenic organisms, whilst limiting the impact of such methods on the environment. With the world's population increasing, there remains a need to generate even more efficient methods for maximising the output from the world's increasingly valuable and precious agricultural land.

It has now surprisingly been found that increasing the amount of 2R, 4S isomer of difenoconazole in the composition, can reduce/prevent the phytotoxic effect of the difenoconazole, whilst retaining the fungicidal effect. Increasing the % by weight of the 2R, 4S isomer therefore provides for a "safening" effect of the difenoconazole allowing it to be applied to the plants at levels which provide for excellent control of phytopathogenic fungi, whilst not being detrimental to the plant's health or appearance. Moreover, in many cases, the compositions according to the invention provide excellent control of phytopathogenic fungi and, also enhance the plant's health or appearance.

According to the present invention there is provided a fungicidal composition which comprises difenoconazole characterised in that at least 40% by weight of said difenoconazole is the 2R, 4S isomer depicted as formula (Ib):

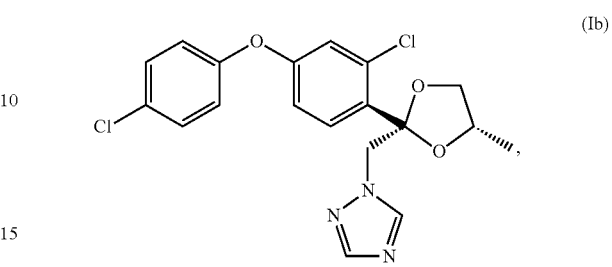

(Ib)

and wherein at least 95% by weight of the remaining difenoconazole is the 2S, 4S isomer depicted as formula (Id):

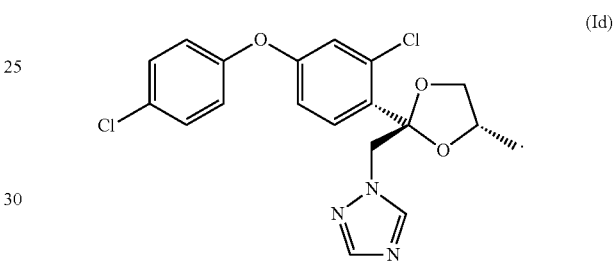

(Id)

Further preferred is a fungicidal composition as described above wherein all of said remaining difenoconazole is said 2S, 4S isomer depicted as formula (Id).

In a further embodiment of the present invention the fungicidal composition comprises at least 55%, or at least 60%, or at least 65%, or at least 80% by weight of said difenoconazole is the "R, 4S isomer depicted as formula (Ib), and preferably all of said remaining difenoconazole is said 2S, 4S isomer depicted as formula (Id).

Difenoconazole (1-[2-[2-chloro-4-(4-chlorophenoxyl) phenyl]-4-methyl-1,3-dioxolan-2-ylmethyl]-1H-1,2,4-triazole) is a fungicide which is effective against a number of diseases caused by Ascomycetes, Basidiomycetes and Deuteromycetes. Difenoconazole is described in "The Pesticide Manual" [The Pesticide Manual—A World Compendium; Fourteenth Edition; Editor: C. D. S. Tomlin; The British Crop Protection Council] under the entry number 253.

Difenoconazole isomers are known to the skilled person as follows:

2S, 4R (cis):

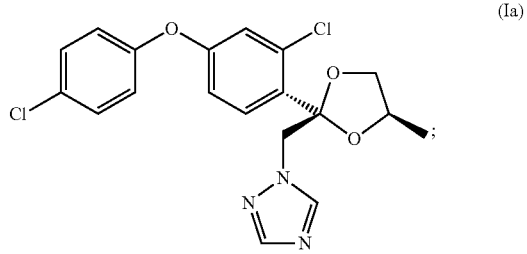

(Ia)

2R, 4S (cis):

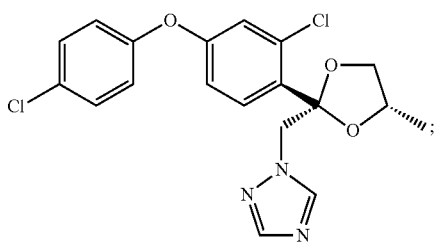

2R, 4R (trans):

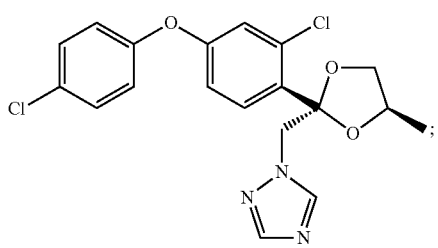

2S, 4S (trans):

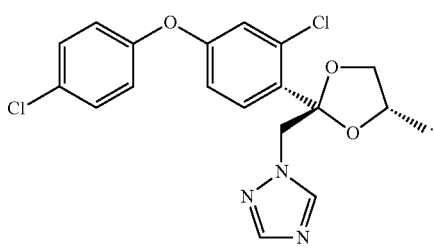

During manufacture, difenoconazole is normally produced in a ratio of about 60:40 cis:trans, with a ratio of 1:1 between cis and trans racemates, i.e. 60:40 2S, 4R (Ia) and 2R, 4S (Ib): 2R, 4R (Ic) and 2S, 4S (Id); and 1:1 of 2S,4R (Ia): 2R, 4S (Ib) and 1:1 2R, 4R (Ic): 2S, 4S (Id). In typical manufacture, the resulting difenoconazole contains about 30% (Ia), about 30% (Ib), about 20% (Ic) and about 20% (Id). An example of this is the product Score 250EC™.

We have now surprisingly identified that by increasing the amount of the isomer (Ib) in the difenoconazole isomeric mixture, the resulting product remains fungicidal but also exhibits reduced phytotoxic effects when applied to plants or propagation material.

The "reduced phytotoxic effect" can be measured by comparison with a control-like plant/propagation material which has been treated with the same amount of difenoconazole but wherein the amount of the 2R, 4S isomer depicted as formula (Ib) is present at less than the % present in a composition according to the invention. The person skilled in the art is well aware how to perform properly controlled experiments and thus can make a comparison assessment by growing two groups of plants of the same species/variety under the same conditions wherein one of said groups (being the plant, or propagation material) has been treated with a composition containing difenoconazole with the 2R, 4S isomer at a % by weight according to the invention, such as 51% or higher, and the control-like group has been treated with a composition containing difenoconazole with the 2R, 4S isomer at a % by weight not according to the invention, such as 30% thereby enabling said skilled person to ascertain the reduction/prevention of the phytotoxic effect. The same applies to a comparison assessment involving any of the other compositions according to the invention. In each case, the comparison will involve using a composition having the characteristics according to the invention with a like composition which contains the same amount of difenoconazole but wherein the amount of the 2R, 4S isomer depicted as formula (Ib) is present at less than the % of any composition according to the invention. For example, the comparison could be made between difenoconazole according to the prior art containing 30% (Ia), 30%(Id), 20% (Ic) and 20% (Id) and difenoconazole according to the invention which contains, say, 60% (Ib) and 40% (Id) only, wherein the test is carried out on like plants under the same conditions and wherein the difenoconazole is applied at the same rate, only the % of isomers differs between the two samples.

Where the composition according to the invention is applied to plant propagation material the reduced phytotoxic effect can be observed on the propagation material and/or the plant which results therefrom. For example, where the composition according to the invention is applied to a seed, the plant, particularly the initial plantlet which results from the germination of the seed, demonstrates the reduced phytotoxic effect of the composition according to the invention.

The skilled person will appreciate that in the compositions according to the invention there may well be very small amounts of "impurities" of the other isomers present, for example, impurities of unwanted difenoconazole isomers up to about 0.5% by weight of the difenoconazole. Thus, the skilled person will appreciate that a composition according to the invention which is stated as comprising, say, 80% of the 2R, 4S isomer depicted as formula (Ib) and 20% of the 2S, 4S isomer depicted as formula (Id) by weight of the difenoconazole could contain about 0.5% of the 2S, 4R isomer depicted as formula (Ia) and/or the 2R, 4R isomer depicted as formula (Ic).

Furthermore, the skilled person will appreciate that when producing compositions according to the invention which contain the enriched isomers as described in this specification, such production processes can be extremely expensive. Whilst it may be preferable to produce a composition which contains predominantly or solely the 2R, 4S isomer depicted as formula (Ib), it can also be preferable to generate a composition which still comprises the 2R, 4S isomer depicted as formula (Ib) in amounts which confer the reduced phytotoxic effect according to the invention in a much more cost economical manner. With this in mind, in a particular aspect of the present invention there is provided a composition which comprises about 60% by weight of the 2R, 4S isomer depicted as formula (Ib) and about 40% by weight of the 2S, 4S isomer depicted as formula (Id).

In a still further aspect of the present invention there is provided a fungicidal composition which comprises difenoconazole characterised in that at least 40% by weight of said difenoconazole is the 2R, 4S isomer depicted as formula (Ib) and wherein at least 50% by weight of the remaining difenoconazole is the 2S, 4S isomer depicted as formula (Id) above.

An example of such a composition is one which comprises, say, 40% of the 2R, 4S isomer of difenoconazole depicted as formula (Ib) and 50% by weight of the remaining difenoconazole is the 2S, 4S isomer depicted as formula (Id), thus 30% of the 2S, 4R isomer is also present in the composition, the remaining 30% being the 2S, 4R isomer of formula (Ia) and/or the 2R, 4R isomer of formula (Ic).

The present invention still further provides a composition as defined above characterised in that at least a % by weight of said difenoconazole is the 2R, 4S isomer depicted as formula (Ib), wherein said % is selected, in order of increasing preference from: 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% and at least 50% by weight of the remaining difenoconazole is the 2S, 4S isomer depicted as formula (Id), more preferably at least 90% by weight of the remaining difenoconazole is the 2S, 4S isomer depicted as formula (Id), more preferably at least 95% by weight of the remaining difenoconazole is the 2S, 4S isomer depicted as formula (Id), more preferably all of the remaining difenoconazole by weight is the 2S, 4S isomer depicted as formula (Id).

The present invention still further provides a fungicidal composition as described above wherein, in increasing order of preference at least 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% 99% and 100% by weight of the remaining difenoconazole is the 2S, 4S isomer depicted as formula (Id). Thus in one embodiment the composition contains 99% by weight of the 2R, 4S isomer depicted as formula (Ib) and 1% by weight of the 2S, 4S isomer depicted as formula (Id). Likewise, in a further embodiment the composition contains 98% by weight of the 2R, 4S isomer depicted as formula (Ib) and 2% by weight of the 2S, 4S isomer depicted as formula (Id). As mentioned above, in a preferred embodiment of the invention the composition contains about 60% by weight of the 2R, 4S isomer depicted as formula (Ib) and about 40% by weight of the 2S, 4S isomer depicted as formula (Id).

Also disclosed are the following combinations of % by weight of the 2R, 4S isomer depicted as formula (Ib) and % by weight of the 2S, 4S isomer depicted as formula (Id):
97% (Ib) and 3% (Id), 96% (Ib) and 4% (Id), 95% (Ib) and 5% (Id), 94% (Ib) and 6% (Id), 93% (Ib) and 7% (Id), 92% (Ib) and 8% (Id), 91% (Ib) and 9% (Id), 90% (Ib) and 10% (Id), 89% (Ib) and 11% (Id), 88% (Ib) and 12% (Id), 87% (Ib) and 13% (Id), 86% (Ib) and 14% (Id), 85% (Ib) and 15% (Id), 84% (Ib) and 16% (Id), 83% (Ib) and 17% (Id), 82% (Ib) and 18% (Id), 81% (Ib) and 19% (Id), 80% (Ib) and 20% (Id), 79% (Ib) and 21% (Id), 78% (Ib) and 22% (Id), 77% (Ib) and 23% (Id), 76% (Ib) and 24% (Id), 75% (Ib) and 25% (Id), 74% (Ib) and 26% (Id), 73% (Ib) and 27% (Id), 72% (Ib) and 28% (Id), 71% (Ib) and 29% (Id), 70% (Ib) and 30% (Id), 69% (Ib) and 31% (Id), 68% (Ib) and 32% (Id), 67% (Ib) and 33% (Id), 66% (Ib) and 34% (Id), 65% (Ib) and 35% (Id), 64% (Ib) and 36% (Id), 63% (Ib) and 37% (Id), 62% (Ib) and 38% (Id), 61% (Ib) and 39% (Id), 60% (Ib) and 40% (Id), 59% (Ib) and 41% (Id), 58% (Ib) and 42% (Id), 57% (Ib) and 43% (Id), 56% (Ib) and 44% (Id), 55% (Ib) and 45% (Id), 54% (Ib) and 46% (Id), 53% (Ib) and 47% (Id), 52% (Ib) and 48% (Id), 51% (Ib) and 49% (Id), 50% (Ib) and 50% (Id), 49% (Ib) and 51%(Id), 48% (Ib) and 52%(Id), 47% (Ib) and 53%(Id), 46% (Ib) and 54%(Id), 45% (Ib) and 55%(Id), 44% (Ib) and 56%(Id), 43% (Ib) and 57%(Id), 42% (Ib) and 58%(Id), 41% (Ib) and 59%(Id), and 40% (Ib) and 60%(Id).

In a still further aspect the present invention also provides a fungicidal composition which comprises difenoconazole characterised in that at least 51% by weight of said difenoconazole is the 2R, 4S isomer depicted as formula (Ib):

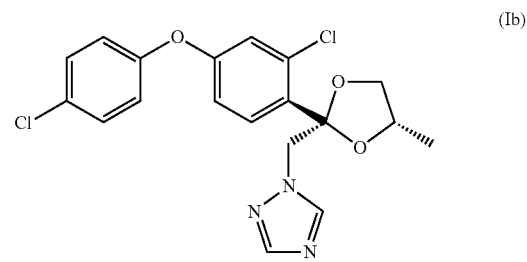

In a further embodiment of the invention said composition is characterised in that at least a % by weight of said difenoconazole is the 2R, 4S isomer depicted as formula (Ib), wherein said % is selected from, in order of increasing preference: 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99%. In a particular embodiment of the invention said composition comprises 100% of the 2R, 4S isomer depicted as formula (Ib).

In a further aspect of the present invention there is provided a fungicidal composition which comprises difenoconazole characterised in that at least 40% by weight of said difenoconazole is the 2R, 4S isomer depicted as formula (Ib) and wherein at least 1% by weight of the remaining difenoconazole is the 2S, 4S isomer depicted as formula (Id) or the 2R, 4R isomer depicted as formula (Ic) above. In a particular embodiment of the invention said composition is characterised in that at least a % by weight of said difenoconazole is the 2R, 4S isomer depicted as formula (Ib), wherein said % is selected from 45% to 85%. In a further embodiment of the invention said composition is characterised in that at least a % by weight of said difenoconazole is the 2R, 4S isomer depicted as formula (Ib), wherein said % is selected from 50% to 80%. In a still further embodiment of the invention said composition is characterised in that at least a % by weight of said difenoconazole is the 2R, 4S isomer depicted as formula (Ib), wherein said % is selected from 55% to 75%. In a still further embodiment of the invention said composition is characterised in that at least a % by weight of said difenoconazole is the 2R, 4S isomer depicted as formula (Ib), wherein said % is selected from 60% to 70%. All of the compositions described in this paragraph contain at least 1% by weight of the 2S, 4S isomer depicted as formula (Id) or the 2R, 4R isomer depicted as formula (Ic) above. In a further embodiment of the invention, the compositions described in this paragraph contain at least 5% by weight of the 2S, 4S isomer depicted as formula (Id) or the 2R, 4R isomer depicted as formula (Ic) above.

The present invention still further provides a fungicidal composition as described above which further comprises one or more components selected from the group consisting of: adjuvant, carrier and surfactant.

The formulation adjuvants that are suitable for the preparation of the compositions according to the invention are known per se. As liquid carriers there may be used: water, toluene, xylene, petroleum ether, vegetable oils, acetone, methyl ethyl ketone, cyclohexanone, acid anhydrides, acetonitrile, acetophenone, amyl acetate, 2-butanone, butylene carbonate, chlorobenzene, cyclohexane, cyclohexanol, alkyl esters of acetic acid, diacetone alcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethylformamide, dimethyl sulfoxide, 1,4-dioxane, dipropylene glycol, dipropylene glycol methyl ether, dipropylene glycol dibenzoate, diproxitol, alkylpyrrolidone, ethyl acetate, 2-ethylhexanol, ethylene carbonate, 1,1,1-trichloroethane, 2-heptanone, alpha-pinene, d-limonene, ethyl lactate, ethylene glycol, ethylene glycol butyl ether, ethylene glycol methyl ether, gamma-butyrolactone, glycerol, glycerol acetate, glycerol diacetate, glycerol triacetate, hexadecane, hexylene glycol, isoamyl acetate, isobornyl acetate, isooctane, isophorone, isopropylbenzene, isopropyl myristate, lactic acid, laurylamine, mesityl oxide, methoxypropanol, methyl isoamyl ketone, methyl isobutyl ketone, methyl laurate, methyl octanoate, methyl oleate, methylene chloride, m-xylene, n-hexane, n-octylamine, octadecanoic acid, octylamine acetate, oleic acid, oleylamine, o-xylene, phenol, polyethylene glycol, propionic acid, propyl lactate, propylene carbonate, propylene glycol, propylene glycol methyl ether, p-xylene, toluene, triethyl phosphate, triethylene glycol, xylenesulfonic acid, paraffin, mineral oil, trichloroethylene, perchloroethylene, ethyl acetate, amyl acetate, butyl acetate, propylene glycol methyl ether, diethylene glycol methyl ether, methanol, ethanol, isopropanol, and alcohols of higher molecular weight, such as amyl alcohol, tetrahydrofurfuryl alcohol, hexanol, octanol, ethylene glycol, propylene glycol, glycerol, N-methyl-2-pyrrolidone and the like.

Suitable solid carriers are, for example, talc, titanium dioxide, pyrophyllite clay, silica, attapulgite clay, kieselguhr, limestone, calcium carbonate, bentonite, calcium montmorillonite, cottonseed husks, wheat flour, soybean flour, pumice, wood flour, ground walnut shells, lignin and similar substances.

A large number of surface-active substances can advantageously be used in both solid and liquid formulations, especially in those formulations which can be diluted with a carrier prior to use. Surface-active substances may be anionic, cationic, non-ionic or polymeric and they can be used as emulsifiers, wetting agents or suspending agents or for other purposes. Typical surface-active substances include, for example, salts of alkyl sulfates, such as diethanolammonium lauryl sulfate; salts of alkylarylsulfonates, such as calcium dodecylbenzenesulfonate; alkylphenol/alkylene oxide addition products, such as nonylphenol ethoxylate; alcohol/alkylene oxide addition products, such as tridecylalcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryltrimethylammonium chloride, polyethylene glycol esters of fatty acids, such as polyethylene glycol stearate; block copolymers of ethylene oxide and propylene oxide; and salts of mono- and di-alkylphosphate esters; and also further substances described e.g. in McCutcheon's Detergents and Emulsifiers Annual, MC Publishing Corp., Ridgewood N.J. (1981).

Further adjuvants that can be used in pesticidal formulations include crystallisation inhibitors, viscosity modifiers, suspending agents, dyes, anti-oxidants, foaming agents, light absorbers, mixing auxiliaries, antifoams, complexing agents, neutralising or pH-modifying substances and buffers, corrosion inhibitors, fragrances, wetting agents, take-up enhancers, micro-nutrients, plasticisers, glidants, lubricants, dispersants, thickeners, antifreezes, microbicides, and liquid and solid fertilisers.

The compositions according to the invention can include an additive comprising an oil of vegetable or animal origin, a mineral oil, alkyl esters of such oils or mixtures of such oils and oil derivatives. The amount of oil additive in the composition according to the invention is generally from 0.01 to 10%, based on the mixture to be applied. For example, the oil additive can be added to a spray tank in the desired concentration after a spray mixture has been prepared. Preferred oil additives comprise mineral oils or an oil of vegetable origin, for example rapeseed oil, olive oil or sunflower oil, emulsified vegetable oil, alkyl esters of oils of vegetable origin, for example the methyl derivatives, or an oil of animal origin, such as fish oil or beef tallow. Preferred oil additives comprise alkyl esters of C8-C22 fatty acids, especially the methyl derivatives of C12-C18 fatty acids, for example the methyl esters of lauric acid, palmitic acid and oleic acid (methyl laurate, methyl palmitate and methyl oleate, respectively). Many oil derivatives are known from the Compendium of Herbicide Adjuvants, 10th Edition, Southern Illinois University, 2010.

In a still further aspect of the present invention there is provided a plant or propagation material which has been treated with a composition according to the invention.

In a still further aspect of the present invention there is provided a treated plant or treated propagation material which results following treatment with the composition according to the invention. The invention therefore extends to a plant or propagation material which comprises the composition according to the invention.

In a still further aspect of the invention there is provided a method for controlling fungi on a plant or propagation material comprising applying to said plant or propagation material a fungicidally effective amount of a composition according to the invention.

In a still further aspect of the present invention there is provided a method for controlling fungi on a plant or propagation material with a composition which has a reduced phytotoxic effect on said plant or propagation material said method comprising applying to said plant or propagation material a fungicidally effective amount of a composition according to the invention.

In a still further aspect of the present invention there is provided a method as described above wherein said composition containing difenoconazole according to the invention is applied to a locus where the plant propagation material is sown/placed and/or where the plant is grown.

The present invention still further provides a method as described above wherein said plant or said plant propagation material is a cereal plant or cereal plant propagation material. In a particular embodiment of the invention said cereal plant or said cereal plant propagation material is wheat. In a further embodiment of the invention said cereal plant or said cereal plant propagation material is barley.

In a still further aspect of the invention there is provided a method for manufacturing difenoconazole which is fungicidally effective whilst having a reduced phytotoxic effect when applied to a plant or propagation material said method comprising manufacturing difenoconazole such that at least 51% by weight of difenoconazole manufactured is the 2R, 4S isomer depicted as formula (Ib) above.

The present invention still further provides a method as described above wherein said phytotoxic effect causes a yellowing and/or browning of the leaves of the plant. "Phytotox" is known to the person skilled in the art. Chlorosis can be described as "paling of the plant tissue due to disruption of chlorophyll production to a lighter green, yellow or white seen across the whole leaf area or in spots or patches". Necrosis can be described as "death of the plant tissue which is observed as brown areas of the leaf, often in spots or patches."

In a still further aspect of the invention there is provided a method for manufacturing difenoconazole characterised in that at least 51% by weight of difenoconazole manufactured is the 2R, 4S isomer depicted as formula (Ib) above.

In a further embodiment of the invention there is provided a method for manufacturing difenoconazole according to the invention as described above.

In a still further aspect of the invention there is provided a method for manufacturing difenoconazole characterised in that least 40% by weight of difenoconazole manufactured is the 2R, 4S isomer depicted as formula (Ib) above and wherein at least 90% by weight of the remaining difenoconazole manufactured is the 2S, 4S isomer depicted as formula (Id) above. In a preferred embodiment of the invention all of said remaining difenoconazole manufactured is the 2S, 4S isomer depicted as formula (Id) above.

In a still further embodiment of the invention there is provided a method for manufacturing difenoconazole said method comprising manufacturing difenoconazole which comprises the amounts by weight of the isomers as described above according to the invention.

Difenoconazole as a mixture of the 4 isomers (Ia), (Ib), (Ic) and (Id) is commercially available. The separation of these 4 isomers is possible, for example, using high-performance liquid chromatography over a chiral stationary phase. The skilled person is well aware how to separate stereoisomers using standard techniques well known in the art.

In a more efficient approach the skilled person may use commercially available pure (2S)-propane-1,2-diol and react it with 1-[2-chloro-4-(4-chlorophenoxyl)phenyl]ethanone following synthesis procedures analogous to those described in U.S. Pat. No. 5,266,585 (examples 5a, 5b and 6). The resulting crude mixture of mainly the compounds Ib and Id can then be easily purified and separated by standard column chromatography over silica. With these purified diastereomers the mixtures described in this specification can be prepared.

In a still further aspect of the invention there is provided the use of a composition which comprises according to the invention as described above in a method for controlling fungi on a plant or plant propagation material thereof wherein said composition has a reduced phytotoxic effect on said plant.

In a further embodiment of the invention there is provided the use as described above wherein said composition comprises at least 60% by weight of the 2R, 4S isomer of depicted as (Ib) and the remaining difenoconazole is the 2S, 4S isomer depicted as formula (Id). Thus, such a composition comprises for example 60% by weight of the 2R, 4S isomer of depicted as (Ib) and 40% by weight of the 2S, 4S isomer depicted as formula (Id).

In a still further embodiment of the invention there is provided the use as described above wherein said composition comprises at least 80% by weight of the 2R, 4S isomer of depicted as (Ib) and the remaining difenoconazole is the 2S, 4S isomer depicted as formula (Id). Thus, such a composition comprises for example 80% by weight of the 2R, 4S isomer of depicted as (Ib) and 20% by weight of the 2S, 4S isomer depicted as formula (Id).

The methods and uses described in this specification all encompass the difenoconazole containing composition as described above according to the invention.

When in use, any composition containing difenoconazole according to the invention may also comprise additional active ingredients, e.g. insecticide, a fungicide, nematicide, synergist, herbicide, plant growth regulator or a "plant health" promoting compound. Examples of active ingredients that can be added to the difenoconazole containing composition include all compounds listed in The Pesticide Manual (British Crop Production Council—ISBN No. 9781901396188) available at www.bcpc.orq.

The difenoconazole according to the invention is of particular use in a composition, or in combination, with the following active ingredients—The numbers in parenthesis below mainly refer to the entry in The Pesticide Manual —Thirteenth Edition:

azoxystrobin (47), dimoxystrobin (226), fluoxastrobin (382), kresoxim-methyl (485), metominostrobin (551), orysastrobin, picoxystrobin (647), pyraclostrobin (690), trifloxystrobin (832), a compound of formula B-1.1

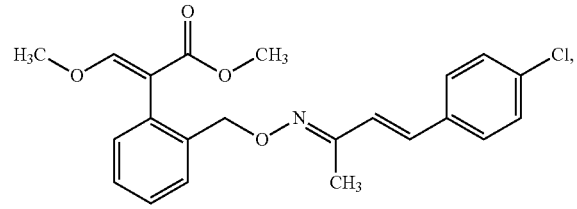

(B-1.1)

azaconazole (40), bromuconazole (96), cyproconazole (207), diniconazole (267), diniconazole-M (267), epoxiconazole (298), fenbuconazole (329), fluquinconazole (385), flusilazole (393), flutriafol (397), hexaconazole (435), imazalil (449), imibenconazole (457), ipconazole (468), metconazole (525), myclobutanil (564), oxpoconazole (607), pefurazoate (618), penconazole (619), prochloraz (659), propiconazole (675), prothioconazole (685), simeconazole (731), tebuconazole (761), tetraconazole (778), triadimefon (814), triadimenol (815), triflumizole (834), triticonazole (842), diclobutrazol (1068), etaconazole (1129), furconazole (1198), furconazole-cis (1199) and quinconazole (1378); aldimorph (CAS Reg. No. 91315-15-0), dodemorph (288), fenpropimorph (344), tridemorph (830), fenpropidin (343), spiroxamine (740), piperalin (648), a compound of formula B-3.1

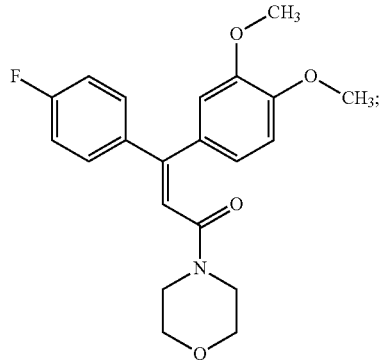

(B-3.1)

cyprodinil (208), mepanipyrim (508), pyrimethanil (705), anilazine (878), benalaxyl (56), benalaxyl-M, benodanil (896), benomyl (62), benthiavalicarb, benthiavalicarb-isopropyl (68), biphenyl (81), bitertanol (84), blasticidin-S (85), bordeaux mixture (87), boscalid (88), bupirimate (98), cadmium chloride, captafol (113), captan (114), carbendazim (116), carbon disulfide (945), carboxin (120), carpropamid (122), cedar leaf oil, chinomethionat (126), chloroneb (139), chlorothalonil (142), chlozolinate (149), cinnamaldehyde, copper, copper ammoniumcarbonate, copper hydroxide (169), copper octanoate (170), copper oleate, copper sulphate (87), cyazofamid (185), cycloheximide (1022), cymoxanil (200), dichlofluanid (230), dichlone (1052), dichloropropene (233), diclocymet (237), diclomezine (239), dicloran (240), diethofencarb (245), diflumetorim (253), dimethirimol (1082), dimethomorph (263), dinocap (270), dithianon (279), dodine (289), edifenphos (290), ethaboxam (304), ethirimol (1133), etridiazole (321), famoxadone (322), fenamidone (325), fenaminosulf (1144), fenamiphos (326), fenarimol (327), fenfuram (333), fenhexamid (334), fenoxanil (338), fenpiclonil (341), fentin acetate (347), fentin chloride, fentin hydroxide (347), ferbam (350), ferimzone (351), fluazinam (363), fludioxonil (368), flusulfamide (394), flutolanil (396), folpet (400), formaldehyde (404), fosetyl-aluminium (407), fthalide (643), fuberidazole (419), furalaxyl (410), furametpyr (411), flyodin (1205), fuazatine (422), hexachlorobenzene (434), hymexazole, iminoctadine tris(albesliate) (CAS Reg. No: 99257-43-9), iodocarb (3-Iodo-2-propynyl butyl carbamate), iprobenfos (IBP) (469), iprodione (470), iprovalicarb (471), isoprothiolane (474), kasugamycin (483), mancozeb (496), maneb (497), manganous dimethyldithiocarbamate, mefenoxam (Metalaxyl-M) (517), mepronil (510), mercuric chloride (511), mercury, metalaxyl (516), methasulfocarb (528), metiram (546), metrafenone, nabam (566), neem oil (hydrophobic extract), nuarimol (587), octhilinone (590), ofurace (592), oxadixyl (601), oxine copper (605), oxolinic acid (606), oxycarboxin (608), oxytetracycline (611), paclobutrazole (612), paraffin oil (628), paraformaldehyde, pencycuron (620), pentachloronitrobenzene (716), pentachlorophenol (623), penthiopyrad, perfurazoate, phosphoric acid, polyoxin (654), polyoxin D zinc salt (654), potassium bicarbonate, probenazole (658), procymidone (660), propamocarb (668), propineb (676), proquinazid (682), prothiocarb (1361), pyrazophos (693), pyrifenox (703), pyroquilon (710), quinoxyfen (715), quintozene (PCN(B) (716), silthiofam (729), sodium bicarbonate, sodium diacetate, sodium propionate, streptomycin (744), sulphur (754), TCMTB, tecloftalam, tecnazene (TCN(B) (767), thiabendazole (790), thifluzamide (796), thiophanate (1435), thiophanate-methyl (802), thiram (804), tolclofos-methyl (808), tolylfluanid (810), triazoxide (821), *trichoderma harzianum* (825), tricyclazole (828), triforine (838), triphenyltin hydroxide (347), validamycin (846), vinclozolin (849), zineb (855), ziram (856), zoxamide (857), 1,1-bis(4-chlorophenyl)-2-ethoxyethanol (IUPAC-Name) (910), 2,4-dichlorophenyl benzenesulfonate (IUPAC-/Chemical Abstracts-Name) (1059), 2-fluoro-N-methyl-N-1-naphthylacetamide (IUPAC-Name) (1295), 4-chlorophenyl phenyl sulfone (IUPAC-Name) (981), a compound of formula B-5.1

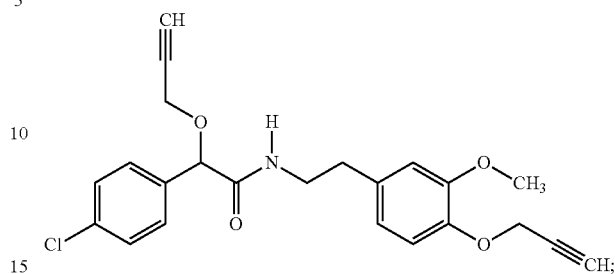

(B-5.1)

a compound of formula B-5.2

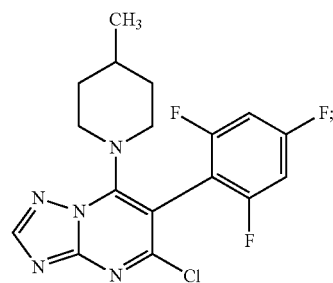

(B-5.2)

a compound of formula B-5.3

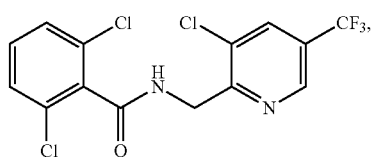

(B-5.3)

a compound of formula B-5.4

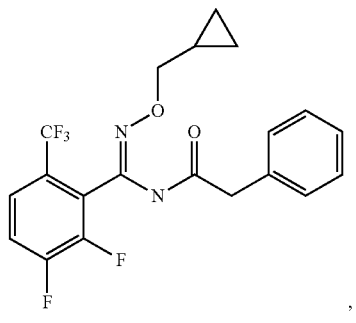

(B-5.4)

a compound of formula B-5.5

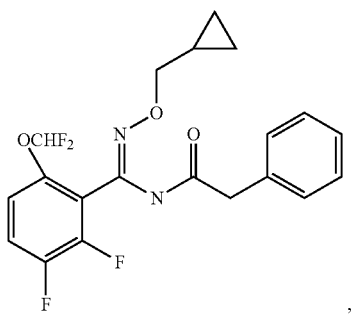
(B-5.5)

a compound of formula B-5.6

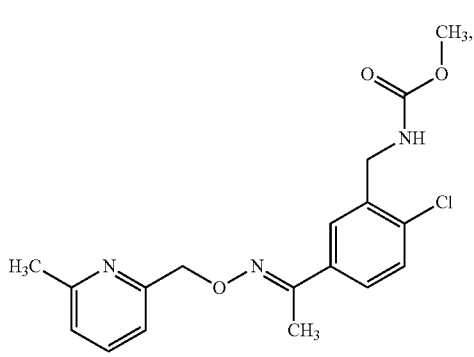
(B-5.6)

a compound of formula B-5.7

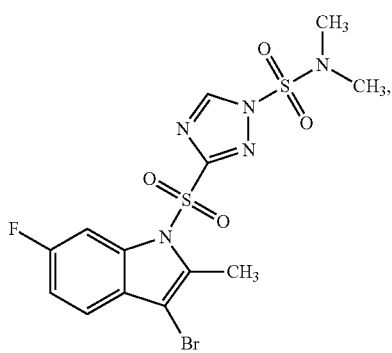
(B-5.7)

3-difluoromethyl-1-methyl-1H-pyrazole-4-carboxylic acid (2-bicyclopropyl-2-yl-phenyl)-amide (compound B-5.8), 3-difluoromethyl-1-methyl-1H-pyrazole-4-carboxylic acid (9-isopropyp-1,2,3,4-tetrahydro-1,4-methano-naphthalen-5-yl)-amide (compound B-5.9), 1,3-dimethyl-5-fluoro-1H-pyrazole-4-carboxylic acid [2-(1,3-dimethylbutyl)phenyl]-amide (compound B-5.10), 3-difluoromethyl-1-methyl-1H-pyrazole-4-carboxylic acid (3',4'-dichloro-5-fluoro-1,1'-biphenyl-2-yl)-amide (compound B-5.11, bixafen), N-{2-[3-chloro-5-(trifluoromethyl)pyridin-2-yl]ethyl}-2-(trifluoromethyl)benzamid (compound B-5.12, fluopyram), 3-difluoromethyl-1-methyl-1H-pyrazole-4-carboxylic acid N-[2-(1,1,2,2-tetrafluoroethoxy)phenyl]-amide (compound B-5.13), 3-difluoromethyl-1-methyl-1H-pyrazole-4-carboxylic acid N-[2-(1,1,2,3,3,3-hexafluoropropoxy)phenyl]-amide (compound B-5.14), 3-difluoromethyl-1-methyl-1H-pyrazole-4-carboxylic acid N-[2-(2-chloro-1,1,2-trifluoroethoxy)phenyl]-amide (compound B-5.15), 3-difluoromethyl-1-methyl-1H-pyrazole-4-carboxylic acid N-(4'-trifluoromethyl-biphen-2-yl)-amide (compound B-5.16), 3-difluoromethyl-1-methyl-1H-pyrazole-4-carboxylic acid N-(2'-trifluoromethyl-biphen-2-yl)-amide (compound B-5.17) and 3-difluoromethyl-1-methyl-1H-pyrazole-4-carboxylic acid N-(2'-trifluoromethyl-biphen-2-yl)-amide (compound B-5.18), acibenzolar-S-methyl (6), chlormequat chloride (137), ethephon (307), mepiquat chloride (509) and trinexapac-ethyl (841), abamectin (1), clothianidin (165), emamectin benzoate (291), imidacloprid (458), tefluthrin (769), thiamethoxam (792), glyphosate (419), a compound of formula V

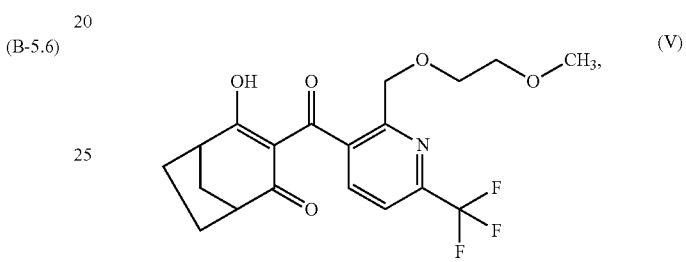
(V)

fomesafen, isopyrazam, sedaxane, a compound of formula (VI)

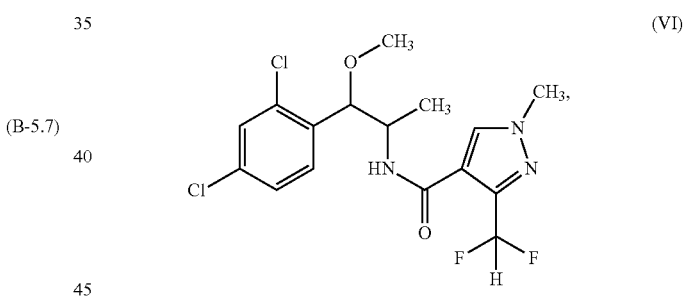
(VI)

a compound of formula (VII)

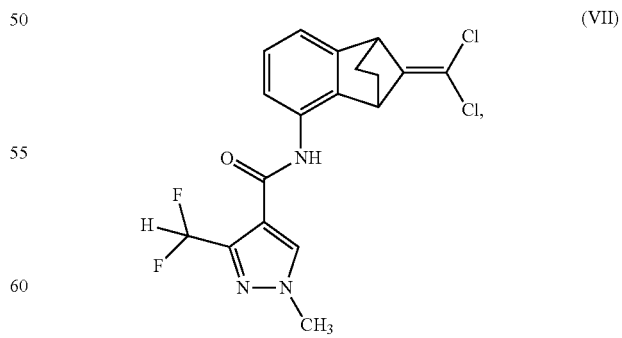
(VII)

1-[4-[4-[(5S)5-(2,6-difluorophenyl)-4,5-dihydro-1,2-oxazol-3-yl]-1,3-thiazol-2-yl]piperidin-1-yl]-2-[5-methyl-3-(trifluoromethyl)-1H-pyrazol-1-yl]ethanone, 1-[4-[4-[5-(2,6-difluorophenyl)-4,5-dihydro-1,2-oxazol-3-yl]-1,3-thiazol- 2-yl]piperidin-1-yl]-2-[5-methyl-3-(trifluoromethyl)-1H-pyrazol-1-yl]ethanone, fluxapyroxad, phosphorous acid, phosphorous acid sodium salt and phosphorous acid ammonium salt.

Preferred mixtures of the difenoconazole according to the invention (referred to in the following lists as difenoconazole) include: difenoconazole and cyproconazole; difenoconazole and propiconazole; difenoconazole and chlorothalonil; difenoconazole and paclobutrazole; difenoconazole and isopyrazam; difenoconazole and azoxystrobin; difenoconazole and azoxystrobin and fludioxonil; difenoconazole and fludioxonil; difenoconazole and cyprodonil; difenoconazole and acibenzolar-s-methyl; difenoconazole and pyraclostrobin; difenoconazole and cyflufenamid; difenoconazole and fenpropidin; difenoconazole and mefenoxam; difenoconazole and thiamethoxam; difenoconazole and metrafenone; difenoconazole and tebuconazole; difenoconazole and penconazole; difenoconazole and epoxiconazole; difenoconazole and prothioconazole; difenoconazole and mefenoxam; difenoconazole and ipconazole; difenoconazole and hexaconazole; difenoconazole and abamectin; difenoconazole and trinexapac; difenoconazole and 1-Methylcyclopropene; difenoconazole and tricyclazole; difenoconazole and lambda cyhalothrin; difenoconazole and S-Metolachlor; difenoconazole and mesotrione; difenoconazole and one of the compounds mentioned in WO2010/063700; difenoconazole and one of the succinate dehydrogenase inhibitor (SDHI) class of fungicides; difenoconazole and benodanil, difenoconazole and flutolanil; difenoconazole and mepronil; difenoconazole and fluopyram; difenoconazole and fenfuram; difenoconazole and carboxin oxycarboxin; difenoconazole and thifluzamide; difenoconazole and bixafen; difenoconazole and furametpyr; difenoconazole and isopyrazam; difenoconazole and penflufen; difenoconazole and penthiopyrad; difenoconazole and sedaxane; difenoconazole and fluxapyroxad and difenoconazole and boscalid.

Even more preferred mixtures according to the invention include: difenoconazole and benzovindiflupyr (benzovindiflupyr is 3-difluoromethyl-1-methyl-1H-pyrazole-4-carboxylic acid (9-dichloromethylene-1,2,3,4-tetrahydro-1,4-methano-naphthalen-5-yl)-amide and its microbicidal properties are described for example in WO 2007/048556); difenoconazole and chlorothalonil; difenoconazole and folpet; difenoconazole and propiconazole; difenoconazole and prothioconazole; difenoconazole and isopyrazam; difenoconazole and fenpropidin; difenoconazole and propiconazole and chlorothalonil; difenoconazole and propiconazole and fenpropidin; difenoconazole and benzovindiflupyr and prothioconazole; difenoconazole and propiconazole and azoxystrobin; difenoconazole and propiconazole and chlorothalonil; difenoconazole and cyproconazole and propiconazole; difenoconazole and propiconazole and folpet; difenoconazole and benzovindiflupyr and chlorothalonil; difenoconazole and benzovindiflupyr and propiconazole; difenoconazole and benzovindiflupyr and isopyrazam; difenoconazole and benzovindiflupyr and azoxystrobin; difenoconazole and benzovindiflupyr and fenpropidin; difenoconazole and benzovindiflupyr and folpet; difenoconazole and benzovindiflupyr and cyproconazole; difenoconazole and benzovindiflupyr and boscalid; difenoconazole and benzovindiflupyr and bixafen; difenoconazole and benzovindiflupyr and penthiopyrad; and difenoconazole and benzovindiflupyr and fluxapyroxad. Particularly preferred mixtures include difenoconazole and chlorothalonil, difenoconazole and chlorothalonil and propiconazole, difenoconazole and metconazole and difenoconazole and benzovindiflupyr.

According to a further aspect of the present invention there is provided a combination of difenoconazole according to the invention with a compound selected from the group consisting of: Cloquintocet Mexyl; Abscisic acid; and a compound of formula II

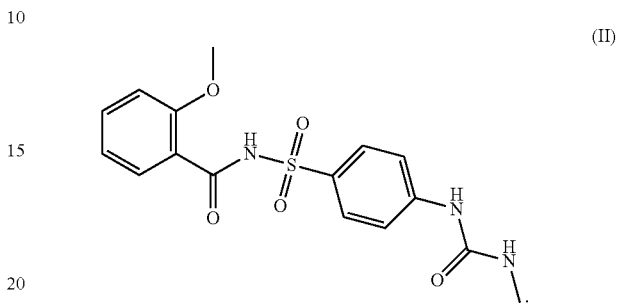

(II)

Cloquintocet-mexyl-(1-methylhexyl [(5-chloro-8-quinolinyl)oxy]acetate) is known as a herbicide safener and is described in "The Pesticide Manual" [The Pesticide Manual—A World Compendium; Fourteenth Edition; Editor: C. D. S. Tomlin; The British Crop Protection Council] under the entry number 166. Whilst Cloquintocet-mexyl is preferred, it is also possible to use alternative Cloquintocet salts and esters in combination with the Difenoconazole in accordance with the present invention. Examples of Cloquintocet salts and esters are known to the person skilled in the art and are described in amongst other things, EP94349; U.S. Pat. No. 4,902,340; and U.S. Pat. No. 5,102,445. Cloquintocet and its salts and esters are therefore also provided in accordance with the present invention and may be used to substitute for or supplement Cloquintocet-mexyl.

Abscisic acid (ABA) is also known as abscisin II and dormin. It has the formula S-(Z,E)]-5-(1-Hydroxy-2,6,6-trimethyl-4-oxo-2-cyclohexen-1-yl)-3-methyl-2,4-pentanedienoic acid:

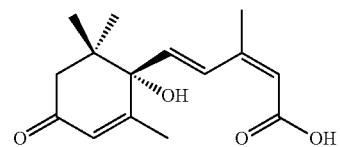

The compound of formula II, namely:

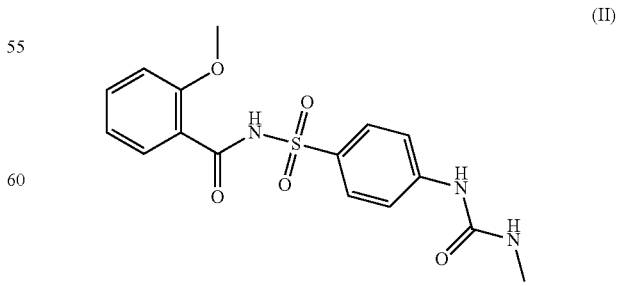

(II)

is described in WO2009/056333 and EP0365484. In the former reference, the compound of formula II is described as a safener for protecting rice crops from the phytotoxic action of herbicides by dressing the seed material with the compound of formula II.

Such a combination as described above can be used in any of the methods as described in this document and the combinations provide a synergistic effect. A synergistic effect exists whenever the action of an active ingredient combination is greater than the sum of the actions of the individual components.

The action to be expected E for a given active ingredient combination obeys the so-called COLBY formula and can be calculated as follows (COLBY, S. R. "Calculating synergistic and antagonistic responses of herbicide combination". Weeds, Vol. 15, pages 20-22; 1967):

ppm=milligrams of active ingredient (=a.i.) per liter of spray mixture

X=% action by active ingredient A) using p ppm of active ingredient

Y=% action by active ingredient B) using q ppm of active ingredient.

According to COLBY, the expected (additive) action of active ingredients A)+B) using p+q ppm of active ingredient is:

$$E = X + Y - \frac{X \cdot Y}{100}$$

If the action actually observed (O) is greater than the expected action (E), then the action of the combination is super-additive, i.e. there is a synergistic effect. In mathematical terms the synergism factor SF corresponds to O/E. In the agricultural practice an SF of ≥1.2 indicates significant improvement over the purely complementary addition of activities (expected activity), while an SF of 0.9 in the practical application routine signals a loss of activity compared to the expected activity.

However, besides the actual synergistic action with respect to fungicidal activity, the compositions according to the invention also have further surprising advantageous properties which can also be described, in a wider sense, as synergistic activity. Examples of such advantageous properties that may be mentioned are: a broadening of the spectrum of fungicidal activity to other phytopathogens, for example to resistant strains; a reduction in the rate of application of the active ingredients; synergistic activity against animal pests, such as insects or representatives of the order Acarina; a broadening of the spectrum of pesticidal activity to other animal pests, for example to resistant animal pests; adequate pest control with the aid of the compositions according to the invention, even at a rate of application at which the individual compounds are totally ineffective; advantageous behavior during formulation and/or upon application, for example upon grinding, sieving, emulsifying, dissolving or dispensing; increased storage stability; improved stability to light; more advantageous degradability; improved toxicological and/or ecotoxicological behavior; improved characteristics of the useful plants including: emergence, crop yields, more developed root system, tillering increase, increase in plant height, bigger leaf blade, less dead basal leaves, stronger tillers, greener leaf colour, less fertilizers needed, less seeds needed, more productive tillers, earlier flowering, early grain maturity, less plant verse (lodging), increased shoot growth, improved plant vigor, and early germination; or any other advantages familiar to a person skilled in the art.

The weight ratio of difenoconazole, being component A):component B—being the compound that the difenoconazole according to the invention may be mixed with) is so selected as to give a synergistic activity. In general the weight ratio of A):B) is, in increasing order of preference, between 2000:1 and 1:2000, 1000:1 and 1:1000, 500:1 and 1:500 100:1 and 1:100, 50:1 and 1:50.

According to the invention "plants" typically comprise the following species of plants: grape vines; cereals, such as wheat, barley, maize, rice, rye or oats; beet, such as sugar beet or fodder beet; fruits, such as pomes, stone fruits or soft fruits, for example apples, pears, plums, peaches, almonds, cherries, strawberries, raspberries or blackberries; leguminous plants, such as beans, lentils, peas or soybeans; oil plants, such as rape, mustard, poppy, olives, sunflowers, coconut, castor oil plants, cocoa beans or groundnuts; cucumber plants, such as marrows, cucumbers or melons; fibre plants, such as cotton, flax, hemp or jute; citrus fruit, such as oranges, lemons, grapefruit or mandarins; vegetables, such as spinach, lettuce, asparagus, cabbages, carrots, onions, tomatoes, potatoes, cucurbits or paprika; lauraceae, such as avocados, cinnamon or camphor; maize; tobacco; nuts; coffee; sugar cane; tea; vines; hops; durian; bananas; natural rubber plants; turf or ornamentals, such as flowers, shrubs, broad-leaved trees or evergreens, for example conifers. This list does not represent any limitation.

Cereals, particularly wheat, rice, maize and barley are of particular interest for the invention, particularly wheat and barley.

The terms "plant" and "plants" also includes plants which have been rendered resistant to herbicides, insecticides, fungicides or have been modified in some other way such as to enhance yield, drought tolerance or quality via conventional methods of breeding or by genetic engineering methods. Any genetically modified plants used in accordance with the present invention may have been modified via recombinant nucleic acid techniques well known to the person skilled in the art.

The term "locus" is intended to embrace the place on which the plants are growing, where the plant propagation materials are sown or where the plant propagation materials will be placed for growth such as a media or soil. An example of a locus is a field, on which crop plants are growing.

The term "plant propagation material" is understood to denote generative parts of the plant, such as seeds, which can be used for the multiplication of the latter, and vegetative material, such as cuttings or tubers, for example, roots, fruits, tubers, bulbs, rhizomes and parts of plants. Germinated plants and young plants which are to be transplanted after germination or after emergence from the soil, are also included in this definition. These young plants may be protected before transplantation by a total or partial treatment by immersion. Preferably "plant propagation material" is understood to denote seeds.

The terms "safening", "safener" and "safen" all relate to the reduced phytotoxic effect of difenoconazole. The term "reduced phytotoxic effect" is defined above.

In a still further aspect, the present invention also provides the composition comprising difenoconazole as described above to provide crop enhancement effects of the resulting plants. In addition to the crop enhancement effects already known for difenoconazole, further crop enhancement effects may be achieved.

The term 'crop enhancement' means an improvement in plant vigour, an improvement in plant quality and/or improved tolerance to stress factors.

According to the present invention, an 'improvement in plant vigour' means that certain traits are improved qualitatively or quantitatively when compared with the same trait in a control plant which has been grown under the same conditions in the absence of the method of the invention. Such traits include, but are not limited to, early and/or improved germination, improved emergence, the ability to use less seeds, increased root growth, a more developed root system, increased root nodulation, increased shoot growth, increased tillering, stronger tillers, more productive tillers, increased or improved plant stand, less plant verse (lodging), an increase and/or improvement in plant height, an increase in plant weight (fresh or dry), bigger leaf blades, greener leaf colour, increased pigment content, increased photosynthetic activity, earlier flowering, longer panicles, early grain maturity, increased seed, fruit or pod size, increased pod or ear number, increased seed number per pod or ear, increased seed mass, enhanced seed filling, less dead basal leaves, delay of senescence, improved vitality of the plant, increased levels of amino acids in storage tissues and/or less inputs needed (e.g. less fertiliser, water and/or labour needed). A plant with improved vigour may have an increase in any of the aforementioned traits or any combination or two or more of the aforementioned traits.

According to the present invention, an 'improvement in plant quality' means that certain traits are improved qualitatively or quantitatively when compared with the same trait in a control plant which has been grown under the same conditions in the absence of the method of the invention. Such traits include, but are not limited to, improved visual appearance of the plant, reduced ethylene (reduced production and/or inhibition of reception), improved quality of harvested material, e.g. seeds, fruits, leaves, vegetables (such improved quality may manifest as improved visual appearance of the harvested material), improved carbohydrate content (e.g. increased quantities of sugar and/or starch, improved sugar acid ratio, reduction of reducing sugars, increased rate of development of sugar), improved protein content, improved oil content and composition, improved nutritional value, reduction in anti-nutritional compounds, improved organoleptic properties (e.g. improved taste) and/or improved consumer health benefits (e.g. increased levels of vitamins and anti-oxidants)), improved post-harvest characteristics (e.g. enhanced shelf-life and/or storage stability, easier processability, easier extraction of compounds) and/or improved seed quality (e.g. for use in following seasons). A plant with improved quality may have an increase in any of the aforementioned traits or any combination or two or more of the aforementioned traits.

According to the present invention, an 'improved tolerance to stress factors' means that certain traits are improved qualitatively or quantitatively when compared with the same trait in a control plant which has been grown under the same conditions in the absence of the method of the invention. Such traits include, but are not limited to, an increased tolerance and/or resistance to abiotic stress factors which cause sub-optimal growing conditions such as drought (e.g. any stress which leads to a lack of water content in plants, a lack of water uptake potential or a reduction in the water supply to plants), cold exposure, heat exposure, osmotic stress, UV stress, flooding, increased salinity (e.g. in the soil), increased mineral exposure, ozone exposure, high light exposure and/or limited availability of nutrients (e.g. nitrogen and/or phosphorus nutrients). A plant with improved tolerance to stress factors may have an increase in any of the aforementioned traits or any combination or two or more of the aforementioned traits. In the case of drought and nutrient stress, such improved tolerances may be due to, for example, more efficient uptake, use or retention of water and nutrients.

Any or all of the above crop enhancements may lead to an improved yield by improving e.g. plant physiology, plant growth and development and/or plant architecture. In the context of the present invention 'yield' includes, but is not limited to, (i) an increase in biomass production, grain yield, starch content, oil content and/or protein content, which may result from (a) an increase in the amount produced by the plant per se or (b) an improved ability to harvest plant matter, (ii) an improvement in the composition of the harvested material (e.g. improved sugar acid ratios, improved oil composition, increased nutritional value, reduction of anti-nutritional compounds, increased consumer health benefits) and/or (iii) an increased/facilitated ability to harvest the crop, improved processability of the crop and/or better storage stability/shelf life. Increased yield of an agricultural plant means that, where it is possible to take a quantitative measurement, the yield of a product of the respective plant is increased by a measurable amount over the yield of the same product of the plant produced under the same conditions, but without application of the present invention. According to the present invention, it is preferred that the yield be increased by at least 0.5%, more preferred at least 1%, even more preferred at least 2%, still more preferred at least 4%, preferably 5% or even more.

Any, or all of, the above crop enhancements may also lead to an improved utilisation of land, i.e. land which was previously unavailable or sub-optimal for cultivation may become available. For example, plants which show an increased ability to survive in drought conditions, may be able to be cultivated in areas of sub-optimal rainfall, e.g. perhaps on the fringe of a desert or even the desert itself.

When applied to the plants in accordance with the use/method of the invention, difenoconazole (a.i.) is typically applied at a rate of 5 to 2000 g a.i./ha, particularly 10 to 1000 g a.i./ha, e.g. 50, 75, 100 or 200 g a.i./ha, 0.5 to 1000 g/ha, preferably 1 to 750 g/ha, more preferably 2.5 to 500 g/ha, more preferably 5 to 300 g/ha, more preferably 7.5 to 200 g/ha of a.i. In a preferred embodiment the difenoconazole according to the invention is applied to crops at a rate up to about 130 g a.i./ha, preferably up to about 125 g a.i./ha.

In agricultural practice the application rates of the compositions according to the use/method of the invention depend on the type of effect desired, and typically range from 20 to 4000 g of total composition per hectare.

When difenoconazole is used for treating seed, rates of 0.001 to 50 g of Difenoconzole per kg of seed, preferably from 0.01 to 10 g per kg of seed, are generally sufficient.

The composition containing difenoconazole according to the invention and any mixtures with other compounds as described above may be employed as a formulation in any conventional form, for example in the form of a twin pack, a powder for dry seed treatment (DS), an emulsion for seed treatment (ES), a flowable concentrate for seed treatment (FS), a solution for seed treatment (LS), a water dispersible powder for seed treatment (WS), a capsule suspension for seed treatment (CF), a gel for seed treatment (GF), an emulsion concentrate (EC), a suspension concentrate (SC), a suspo-emulsion (SE), a capsule suspension (CS), a water dispersible granule (WG), an emulsifiable granule (EG), an emulsion, water in oil (EO), an emulsion, oil in water (EW), a micro-emulsion (ME), an oil dispersion (OD), an oil miscible flowable (OF), an oil miscible liquid (OL), a soluble concentrate (SL), an ultra-low volume suspension (SU), an ultra-low volume liquid (UL), a technical concentrate (TK), a dispersible concentrate (DC), a wettable powder (WP) or any technically feasible formulation in combination with agriculturally acceptable adjuvants.

Such mixtures and compositions may be produced in manner well known to the person skilled in the art, e.g. by mixing the active ingredients with at least one appropriate inert formulation adjuvant (for example, diluents, solvents, fillers and optionally other formulating ingredients such as surfactants, biocides, anti-freeze, stickers, thickeners and compounds that provide adjuvancy effects. Inert ingredients especially biocides must be carefully selected by the person skilled in the art such that they do not inhibit or damage the nitrogen fixing bacteria). Also slow release formulations may be employed where long lasting efficacy is intended. Particularly formulations to be applied in spraying forms, such as water dispersible concentrates (e.g. EC, SC, DC, OD, SE, EW, EO and the like), wettable powders and granules, may contain surfactants such as wetting and dispersing agents and other compounds that provide adjuvancy effects, e.g. the condensation product of formaldehyde with naphthalene sulphonate, an alkylarylsulphonate, a lignin sulphonate, a fatty alkyl sulphate, and ethoxylated alkylphenol and an ethoxylated fatty alcohol.

Formulation ingredients well known to the person skilled in the art may, for example, include those formulation ingredients that do not have any significant biological activity, or have no biological activity. They include, for example, diluents, solvents, fillers, surfactants, biocides, anti-freeze, stickers, thickeners and compounds that provide adjuvancy effects.

A seed dressing formulation is applied in a manner known to the person skilled in the art, e.g. as an aqueous suspension or in a dry powder form having good adherence to the seeds. Such seed dressing formulations are known in the art. Seed dressing formulations may contain the single active ingredients or the combination of active ingredients in encapsulated form, e.g. as slow release capsules or microcapsules. A typical a tank-mix formulation for seed treatment application comprises 0.25 to 80%, especially 1 to 75%, of the desired ingredients, and 99.75 to 20%, especially 99 to 25%, of a solid or liquid auxiliaries (including, for example, a solvent such as water), where the auxiliaries can be a surfactant in an amount of 0 to 40%, especially 0.5 to 30%, based on the tank-mix formulation. A typical pre-mix formulation for seed treatment application comprises 0.5 to 99.9%, especially 1 to 95%, of the desired ingredients, and 99.5 to 0.1%, especially 99 to 5%, of a solid or liquid adjuvant (including, for example, a solvent such as water), where the auxiliaries can be a surfactant in an amount of 0 to 50%, especially 0.5 to 40%, based on the pre-mix formulation.

In general, the formulations include from 0.01 to 90% by weight of active agent, from 0 to 20% agriculturally acceptable surfactant and 10 to 99.99% solid or liquid formulation inerts and adjuvant(s), the active agent consisting of at least difenoconazole as described above and optionally other active agents, including those mentioned above and/or microbiocides or conservatives or the like. Concentrated forms of compositions generally contain in between about 2 and 80%, preferably between about 5 and 70% by weight of active agent. Application forms of formulation may for example contain from 0.01 to 20% by weight, preferably from 0.01 to 5% by weight of active agent. Whereas commercial products will preferably be formulated as concentrates, the end user will normally employ diluted formulations.

The examples which follow serve to illustrate the invention. The invention is not limited to these Examples.

The following products were used in these examples.

Heavy aromatic solvent is Solvesso 200 available from ExxonMobile, Cologne, Germany. Calcium dodecylbenzenesulfonate is Nansa EVM 62/H available from Huntsman Surface Sciences, Castiglione delle Stiviere, Italy. Castor oil 36-ethoxylate is Emulsogen EL360 available from Clariant, Frankfurt, Germany. Oleyl 10-ethoxylate is Genapol O-100 available from Clariant, Frankfurt, Germany. Score 250EC™ is an emulsifiable concentrate formulation containing 250 g/L of difenoconazole and commercially available from Syngenta, Dielsdorf, Switzerland. Score 250EC™ contains said difenoconazole isomers in the following approximate by weight ratio: 2S, 4R (Ia)—30%; 2R, 4S (Ib)—30%; 2R, 4R (Ic) 20%; and 2S, 4S (Id)—20%.

EXAMPLE 1

In a 2 l three necked round bottom 1-[2-chloro-4-(4-chlorophenoxyl)phenyl]ethanone (288.3 g), (2S)-propane-1,2-diol (170.8 g) and p-toluenesulfonic acid (3.3 g) in toluene are heated under reflux on a water separator. After completion of the reaction the solvent and the excess of the propanediol were removed under vacuo.

The crude mixture of the ((Ib) 2R,4S)- and the ((Id) 2S,4S)-methyl dioxolanes was then transformed to the final product following the procedures described in the examples 5b and 6 in U.S. Pat. No. 5,266,585. After the aqueous extraction the solvent was evaporated in vacuo. The resulting crude about 3:2 mixture, of (Ib) and (Id), a viscous oil, was purified according example 2.

EXAMPLE 2

100 g of the crude product obtained in example 1 were dissolved in 2-methoxy-2-methylpropane (100 g) and purified by column chromatography using silica as stationary phase and 2-methoxy-2-methylpropane as eluent. This method delivered about 20 g of (Ib 2R,4S) (cis product) and about 9 g of (Id 2S,4S) (trans product), both in >98% diastereomeric purity.

((Ib) 2R,4S)

1H NMR (300 MHz, CDCl3): $\delta$=1.09 (d, J=6.1 Hz, 3 H), 3.07 (t, J=7.5 Hz, 1 H), 3.9 (dd, J=7.5 Hz, 1 H), 4.07 (dm, J=7.4, 6.1 Hz, 1 H), 4.75 (m, 2 H), 6.8 (dd, J=8.7, 2.5 Hz, 1 H), 6.95 (m, 2 H), 7.0 (d, J=2.5 Hz, 1 H), 7.31 (m, 2 H), 7.54 (d, J=8.7 Hz, 1 H), 7.91 (s, 1 H), 8.24 (s, 1 H).

((Id) 2S,4S)

1H NMR (300 MHz, CDCl3): $\delta$=1.10 (d, J=6.1 Hz, 3 H), 3.24 (t, J=8.2 Hz, 1 H), 3.77 (dm, J=8.2, 6.1 Hz, 1 H), 3.93 (dd, J=6.1, 8.2 Hz, 1 H), 4.67 (m, 2 H), 6.76 (dd, J=8.7, 2.5 Hz, 1 H), 6.92 (m, 2 H), 6.97 (d, J=2.5 Hz, 1 H), 7.26 (m, 2 H), 7.55 (d, J=8.7 Hz, 1 H), 7.83 (s, 1 H), 8.12 (s, 1 H).

EXAMPLE 3

This example shows that the 2R, 4S stereoisomer of difenoconazole (Ib) causes less phytotoxic damage to wheat than the 2S, 4R (Ia), 2R, 4R (Ic) and 2S, 4S (Id) stereoisomers.

Difenoconazole emulsifiable concentrate formulations were prepared containing separately each of the four possible stereoisomers. The following compositions were charged separately to stirred vessels and heated to 80° C. for 1 hour to give clear, yellow liquids.

| Example (in parts by weight) | 3A | 3B | 3C | 3D |
|---|---|---|---|---|
| Difenoconazole | 2S,4R (Ia) 23.7 | 2R,4S (Ib) 23.7 | 2R,4R (Ic) 23.7 | 2S,4S (Id) 23.7 |
| Calcium dodecylbenzenesulfonate | 4.6 | 4.6 | 4.6 | 4.6 |
| Castor oil 36-ethoxylate | 6.5 | 6.5 | 6.5 | 6.5 |
| Oleyl 10-ethoxylate | 3.7 | 3.7 | 3.7 | 3.7 |
| Heavy aromatic solvent | 61.3 | 61.3 | 61.3 | 61.3 |

Wheat seeds (variety "Riband") were sown in 6.5 cm diameter pots with typically 6 seeds per pot. The growing media comprised 66.5% TKS1 peat soil, 30% sugar beet soil and 3.5% sand. The seeds were covered with a fine layer of soil and the pots were watered. Within a day of sowing the pots were treated with 5 mL of a solution of the growth regulator trinexapac-ethyl (Moddus 250 EC™ from Syngenta) diluted 1 part in 1000 parts water. The pots were kept in a controlled environment room at 19° C. constant temperature, 60% relative humidity and a 14 hour day length until test treatment at which time the plants were around 3 weeks old. Plant density was reduced to typically 4 plants per pot prior to application of the test treatments.

The difenoconazole formulations were mixed with water and ultrasonically agitated in order to achieve a homogeneous emulsion. Spray solutions were then made with 9 parts water to 1 part isopropanol by volume. The test treatments were applied using a track-sprayer with a single flat-fan nozzle at a height of 60 cm and calibrated to apply the equivalent of 200 litres per hectare.

The symptoms of phytotoxicity on wheat caused by difenoconazole included chlorosis and/or necrosis. Phytotoxicity was assessed as percentage damage of the plant 14 days after application and the results shown in the following table.

| Example | Difenoconazole | 125 g/ha | 250 g/ha | 500 g/ha |
|---|---|---|---|---|
| 3A | 2S,4R (Ia) | 25 | 40 | 50 |
| 3B | 2R,4S (Ib) | 2.5 | 1.0 | 3.5 |
| 3C | 2R,4R (Ic) | 7.5 | 50 | 60 |
| 3D | 2S,4S (Id) | 5 | 25 | 55 |

EXAMPLE 4

This example shows that the extent of phytotoxic damage to wheat is dependent on the ratio of 2R, 4S difenoconazole (Ib) to 2S, 4S difenoconazole (Id).

Difenoconazole emulsifiable concentrate formulations were prepared containing different ratios of 2R, 4S difenoconazole (Ib) to 2S, 4S difenoconazole (Id). The following compositions were charged separately to stirred vessels and heated to 80° C. for 1 hour to give clear, yellow liquids.

| Example (in parts by weight) | 4A | 4B | 4C | 4D | 4E | 4F |
|---|---|---|---|---|---|---|
| Difenoconazole 2R,4S (Ib) | 9.5 (40%) | 11.8 (50%) | 14.2 (60%) | 16.6 (70%) | 19.0 (80%) | 21.3 (90%) |
| Difenoconazole 2S,4S (Id) | 14.2 (60%) | 11.8 (50%) | 9.5 (40%) | 7.1 (30%) | 4.7 (20%) | 2.4 (10%) |
| Calcium dodecylbenzene sulfonate | 4.6 | 4.6 | 4.6 | 4.6 | 4.6 | 4.6 |
| Castor oil 36-ethoxylate | 6.5 | 6.5 | 6.5 | 6.5 | 6.5 | 6.5 |
| Oleyl 10-ethoxylate | 3.7 | 3.7 | 3.7 | 3.7 | 3.7 | 3.7 |
| Heavy aromatic solvent | 61.3 | 61.3 | 61.3 | 61.3 | 61.3 | 61.3 |

Test wheat plants were grown and the formulations applied as for Example 3. The experimental formulations containing 2R, 4S difenoconazole (Ib) and 2S, 4S difenoconazole (Id) were tested alongside a commercial product, Score 250EC™, which contains all four stereoisomers (Ia, Ib, Ic and Id). The symptoms of phytotoxicity on wheat caused by difenoconazole included chlorosis and/or necrosis. Phytotoxicity was assessed as percentage damage of the plant 14 days after application and the results shown in the following table.

| Example | 100 g/ha | 200 g/ha | 400 g/ha |
|---|---|---|---|
| 4A | 0.5 | 8.0 | 20 |
| 4B | 1.0 | 2.8 | 20 |
| 4C | 0.0 | 1.0 | 7.5 |
| 4D | 0.0 | 1.0 | 10 |
| 4E | 0.5 | 1.0 | 4.3 |
| 4F | 0.0 | 0.0 | 5.5 |
| Score 250EC ™ reference above | 15 | 30 | 45 |

EXAMPLE 5

This example further shows that the extent of phytotoxic damage to wheat is dependent on the ratio of 2R, 4S difenoconazole (Ib) to 2S, 4S difenoconazole.

Test wheat plants were grown and the formulations applied as for Example 3. The experimental formulations containing 2R, 4S difenoconazole (Ib) and 2S, 4S difenoconazole (Id) were tested alongside a commercial product, Score 250EC™, which contains all four stereoisomers (Ia, Ib, Ic and Id). The symptoms of phytotoxicity on wheat caused by difenoconazole included chlorosis and/or necrosis. Phytotoxicity was assessed as percentage damage of the plant 14 days after application and the results shown in the following table.

| Example | 100 g/ha | 200 g/ha | 400 g/ha |
|---|---|---|---|
| 3B (100% Ib) | 0 | 2 | 4 |
| 4F (90% Ib, 10% Id) | 0 | 0 | 5 |
| 4E (80% Ib, 20% Id) | 0 | 1 | 5 |
| 4C (60% Ib, 40% Id) | 2 | 4 | 7 |
| 3D (100% Id) | 2.5 | 15 | 40 |
| Score 250EC ™ reference above | 5 | 13.5 | 40 |

EXAMPLE 6

This example shows that the extent of phytotoxic damage to field grown wheat caused by a formulation with increased content of 2R, 4S difenoconazole is reduced compared with a standard product and that biological performance is equivalent.

The emulsifiable concentrate formulation of example 4C containing 60% 2R, 4S difenoconazole (Ib) and 40% 2S, 4S difenoconazole (Id) was applied to wheat in 11 separate field trials in 4 different countries in Northern Europe alongside a commercial product, Score 250EC™, which contains all four stereoisomers (Ia, Ib, Ic and Id) in the ratios as described above. The products were applied twice, in an equivalent of 200 liters of water per hectare at growth stage BBCH 32 and 39. Phytotoxicity was observed in 8 trials at 7 to 10 days after the first application and was assessed as % leaf damage. *Septoria tritici* infection was observed in 5 trials from growth stage 39 and was assessed on the flag leaf, leaf number 2 and leaf number 3 as percent infection.

| Example | 4C | Score 250EC ™ |
|---|---|---|
| Phytotoxicity @ 250 g/ha (a) | 8 | 14.5 |
| Phytotoxicity @ 125 g/ha (a) | 3 | 8 |
| S. tritici control @ 125 g/ha (b) | 7 | 4 |

(a) Mean % leaf damage from 8 trials
(b) Mean % infection from 5 trials

The invention claimed is:

1. A method for safening the phytotoxic effect of a fungicidal composition which comprises difenoconazole on a plant or plant propagation material said method comprising applying to said plant or plant propagation material a fungicidal composition which comprises difenoconazole wherein at least 40% by weight of said difenoconazole is the 2R, 4S isomer depicted as formula (Ib):

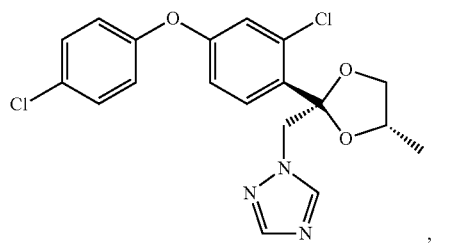

and wherein at least 95% by weight of the remaining difenoconazole is the 2S, 4S isomer depicted as formula (Id):

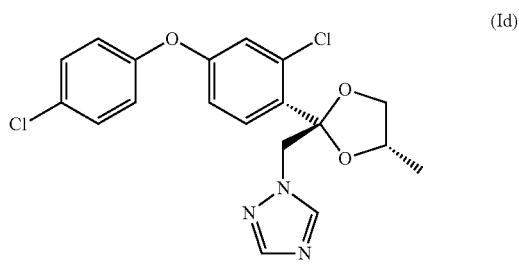

and wherein the safening is measured in comparison to a reference difenoconazole comprising difenoconazole isomers in approximately the weight percentages of: 30% 2S, 4R; 30% 2R, 4S; 20% 2R, 4R; and 20% 2S, 4S.

2. A method according to claim 1 wherein all of said remaining difenoconazole is said 2S, 4S isomer depicted as formula (Id).

3. A method according to claim 1 wherein at least 55% by weight of said difenoconazole in said composition is the 2R, 4S isomer depicted as formula (Ib).

4. A method according to claim 1 wherein at least 60% by weight of said difenoconazole in said composition is the 2R, 4S isomer depicted as formula (Ib).

5. A method according to claim 1 wherein at least 65% by weight of said difenoconazole in said composition is the 2R, 4S isomer depicted as formula (Ib).

6. A method according to claim 1 wherein at least 80% by weight of said difenoconazole in said composition is the 2R, 4S isomer depicted as formula (Ib).

7. A method according to claim 1 wherein said composition further comprises one or more components selected from the group consisting of: adjuvant, carrier and surfactant.

8. A method according to claim 1 wherein said plant or propagation material is a cereal plant or cereal propagation material.

9. A method according to claim 8 wherein said plant or propagation material is wheat or barley.

10. A method according to claim 9 wherein said plant or propagation material is wheat.

11. A method according to claim 9 wherein said plant or propagation material is barley.

* * * * *